Sept. 10, 1974 B. J. MACHIN Plant Pat. 3,616
CHRYSANTHEMUM PLANT
Filed May 29, 1973
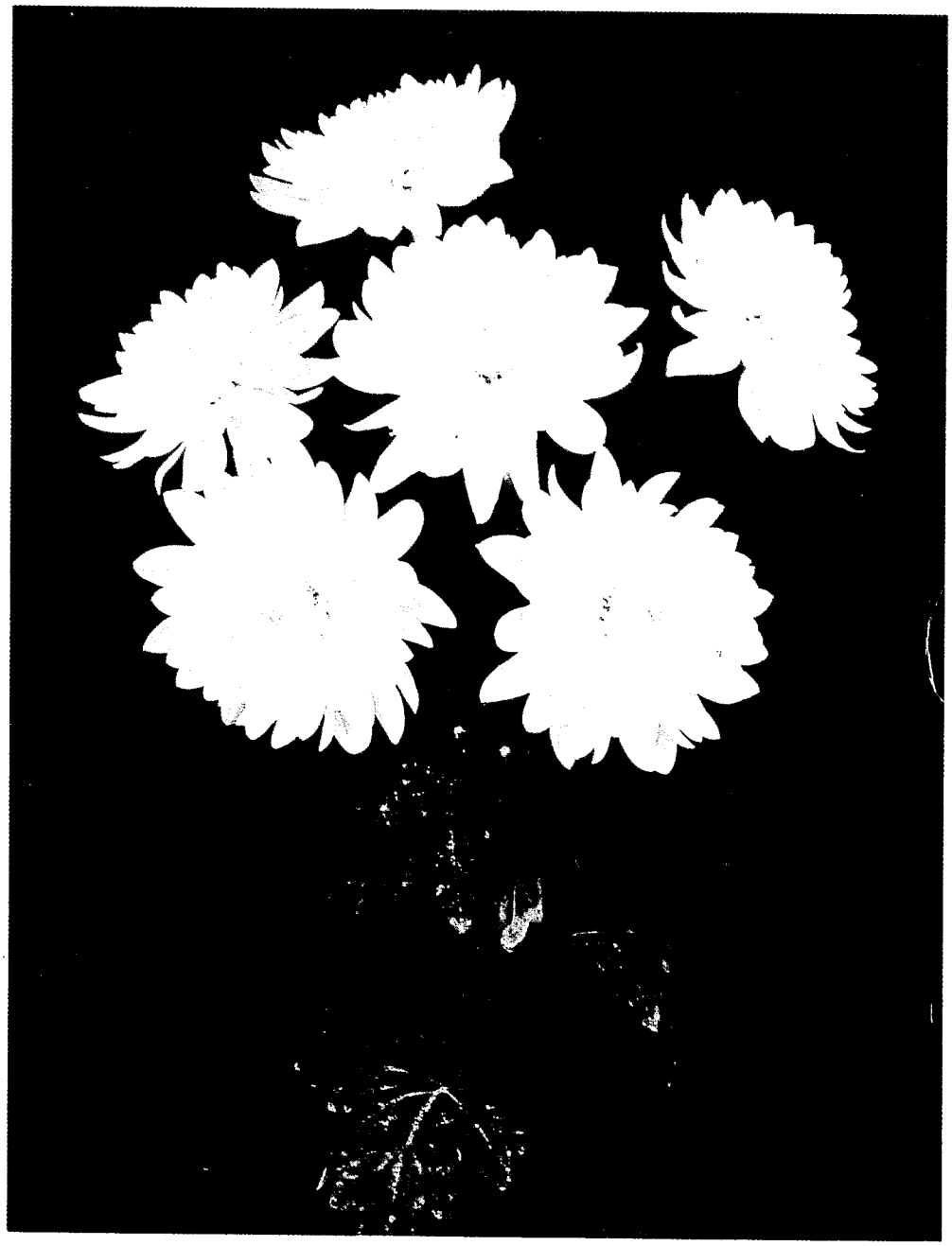

United States Patent Office

Plant Pat. 3,616
Patented Sept. 10, 1974

3,616
CHRYSANTHEMUM PLANT

Barrie John Machin, Chichester, England, assignor to Frampton's Nurseries Limited, Sussex, England Filed May 29, 1973, Ser. No. 364,489
Int. Cl. A01h *5/00*
U.S. Cl. Plt.—78 1 Claim This invention relates to a new and distinct variety of *Chrysanthemum morifolium* Bailey (spray type known as Yellow Arctic.

Yellow Arctic is a sport from the variety Arctic (U.S. Plant Pat. No. 3326) which was originated by me by crossing the variety Saturn, with a seedling known as B4 in 1964, the former being the seed parent and the latter being the pollen parent.

The new variety resulted from an extensive breeding program with the objective of producing an open terminal spray type chrysanthemum dependable under a wide range of controlled year-round and/or natural season growing conditions.

The variety Yellow Arctic is a yellow sport induced by irradiation from the white variety Arctic in June 1971.

The following unique combination of characteristics distinguished Arctic from the most similar existing yellow spray types of which I am aware:

(1) As compared with Improved Yellow Hurricane, Yellow Arctic has:

(a) No clubby sprays (i.e. sprays with very short pedicels) in spring crops.
(b) More vigor, requiring no extra longday growing growing time.
(c) Better breaking action for pinched crops.
(d) No problems due to abortion of the growing points.
(e) More flowers per spray.

(2) As compared with Yellow Iceberg, Yellow Arctic has:

(a) No pinking of the florets when finished in cool temperatures.
(b) No known foliar or stem rot problems.
(c) The ability to initiate and develop flowers in 56° F. minimum night temperatures.
(d) More flowers per spray, resulting in higher market grades.

(3) As compared with Yellow Chip, Yellow Arctic has:

(a) No pinking of the florets when finished in cool temperatures.
(b) Better breaking action for pinched crops.
(c) More flowers per spray, resulting in higher market grades.

Yellow Arctic is distinguished from Arctic by the yellow color of its flower, but apart from flower color the characteristics of Yellow Arctic are similar to those of Arctic.

Asexual reproduction of this new variety, as performed in Sussex, England, shows that the above characteristics are fixed and come true to type through succeeding generations.

The accompanying drawing shows a typical flower of my new variety depicted in color as nearly true as it is reasonably possible to make the same in a color illustration of this type.

The following is a detailed description of the new variety Yellow Arctic with color terminology in accordance with the Royal Horticultural Society Colour Chart (RHS).

Genus—*Chrysanthemum.*
Species—*Morifolium* Bailey.
Type—Spray.
Class—Decorative.
Breeding—Sport from Arctic June 1971.
Propagation—Holds its distinguishing characteristics through succeeding propagations by rooting vegetative shoots.
Flower—Borne on pedicels, 8 to 16 flowers per main stem as a spray type.
Bloom—
*Size.*—2 to 2½ inches in diameter when fully open.
*Petalage.*—Double, 200–250 ray petals. 5 to 10 disc petals.
*Form.*—Decorative and rather flat.
*Petals.*—Thick and broad, overlapping blunt and slightly curled.
*Pedicels.*—Thick and fairly long (4–8 inches), flowers held at an angle of about 60° to the main stem.
Color of Open Bloom:
Inner face of fully expanded petal RHS 7A.
Outer face of fully expanded petal RHS 8B.
Inner face of young petal RHS 7B.
Outer face of young petal RHS 8B.
Response Group (Weeks of short days to flower)—9 weeks.
Temperature tolerance—55–60° F. at night.
Plant—Strong upright habit. Produces 44 inch stems on a single stem crop with five longday weeks.
Foliage—Medium quantity. Average internode length 1 inch. Medium Size.
*Color.*—young leaves RHS 138A; mature leaves RHS 138B. Medium texture.
Stem—
*Thickness.*—thick.
*Strength.*—Strong.
*Color at flowering.*—RHS 138C.
*Water uptake.*—good.

I claim:

1. A new and distinct variety of *Chrysanthemum morifolium* Bailey (spray type) substantially as herein shown and described.

No references cited.

ROBERT E. BAGWILL, Primary Examiner